(12) United States Patent
Enenkel et al.

(10) Patent No.: US 10,295,503 B2
(45) Date of Patent: May 21, 2019

(54) SYSTEM FOR DISPLAY OF NON-DESTRUCTIVE TESTING REGION

(71) Applicant: Zetec, INC., Snoqualmie, WA (US)

(72) Inventors: Laurent Enenkel, Quebec (CA); Frederic Morrow, St. Jean-Chrysostome (CA); Alexandre Charlebois, St. Etienne de Lauzon (CA); Martin Garneau, Quebec (CA); Stephane Turgeon, St. Nicolas (CA)

(73) Assignee: ZETEC, INC., Snoqualmie, WA (US)

( * ) Notice: Subject to any disclaimer, the term of this patent is extended or adjusted under 35 U.S.C. 154(b) by 98 days.

(21) Appl. No.: 15/519,335

(22) PCT Filed: Oct. 15, 2015

(86) PCT No.: PCT/US2015/055683
§ 371 (c)(1),
(2) Date: Apr. 14, 2017

(87) PCT Pub. No.: WO2016/061319
PCT Pub. Date: Apr. 21, 2016

(65) Prior Publication Data
US 2017/0241956 A1    Aug. 24, 2017

Related U.S. Application Data

(60) Provisional application No. 62/065,413, filed on Oct. 17, 2014.

(51) Int. Cl.
*G01N 27/90* (2006.01)
*G01N 29/06* (2006.01)
(Continued)

(52) U.S. Cl.
CPC ....... *G01N 29/226* (2013.01); *G01N 27/9013* (2013.01); *G01N 29/0618* (2013.01);
(Continued)

(58) Field of Classification Search
CPC .......... G01N 27/9013; G01N 29/0618; G01N 29/0636; G01N 29/265; G01N 29/225; G01N 29/226; G01N 29/0645
(Continued)

(56) References Cited

U.S. PATENT DOCUMENTS

| 4,434,660 A | * | 3/1984 | Michaels | G01N 29/265 |
| | | | | 73/619 |
| 5,505,089 A | * | 4/1996 | Weigel | G01N 29/069 |
| | | | | 73/635 |

(Continued)

FOREIGN PATENT DOCUMENTS

| EP | 2 749 879 A2 | 7/2014 |
| JP | 2006 170766 A | 6/2006 |

OTHER PUBLICATIONS

The International Search Report and Written Opinion issued for the corresponding international application No. PCT/US2015/055683, dated Jan. 27, 2016, 11 pages.

*Primary Examiner* — Jacques M Saint Surin
(74) *Attorney, Agent, or Firm* — Snyder, Clark, Lesch & Chung, LLP

(57) ABSTRACT

A system for displaying an area covered in a non-destructive scan of an area larger than the test probe is disclosed. Position encoders are included on the test probe to track the motion of the probe and to provide a record of the portion of the area under test that has been covered by the probe.

11 Claims, 6 Drawing Sheets

(51) Int. Cl.
    *G01N 29/22*     (2006.01)
    *G01N 29/265*    (2006.01)
(52) U.S. Cl.
    CPC ..... *G01N 29/0636* (2013.01); *G01N 29/0645* (2013.01); *G01N 29/225* (2013.01); *G01N 29/265* (2013.01)
(58) Field of Classification Search
    USPC .......................................................... 73/620
    See application file for complete search history.

(56) References Cited

U.S. PATENT DOCUMENTS

| | | | | |
|---|---|---|---|---|
| 5,535,628 | A * | 7/1996 | Rutherford | G01N 29/225 73/622 |
| 2002/0017140 | A1* | 2/2002 | Georgeson | G01N 29/225 73/618 |
| 2013/0304251 | A1* | 11/2013 | Garvey | G01N 29/225 700/213 |
| 2014/0278221 | A1 | 9/2014 | Troy et al. | |

\* cited by examiner

SYSTEM FOR DISPLAY OF NON-DESTRUCTIVE TESTING REGION

CROSS-REFERENCE TO RELATED APPLICATIONS

This PCT application claims the benefit under 35 U.S.C. § 119(e) of U.S. Provisional Application Ser. No. 62/065,413 filed on Oct. 17, 2014, entitled SYSTEM FOR DISPLAY OF NON-DESTRUCTIVE TESTING COVERAGE REGION. The entire disclosure of that application is incorporated by reference herein.

SPECIFICATION

Field of the Invention

The invention relates generally to the field of non-destructive testing.

Background

In the field of non-destructive testing (NDT), and in particular ultrasonic non-destructive testing, it is known to use scanners that survey a large surface area by being moved across the surface area. It can be difficult to keep track of which parts of the surface have been scanned. When performing area scanning (non-destructive examination) a defined surface needs to be covered. The probes (sensing device) used to inspect the area having a smaller surface than the area to be scanned, it is important that the scanning device is tracked so as to provide and guaranty a full surface coverage exempt of gap, and a precise position for every measurement point.

Prior art systems have required manual scanner head adjustment or stitching operations on the acquired non-destructive test data. Two axis encoders are also known, but have not been precise and did not measure device orientation relative to the article being inspected.

A prior art rectangular scanning support is shown in FIG. 1. A rectangular scanning support 20, supporting a scanning head 10 can be operated on a limited and defined surface. It is cumbersome to install and cannot inspect any area outside of the surface 30 defined by the frame. Thus scanning the entire inspection surface 40 becomes a cumbersome task of piecing together several scans of the limited coverage area 30. A prior art R Theta scanner, having a scanner head 201 and scanner base 230 is shown in FIG. 2. Again, the area to inspect 240 is larger than the coverage area 220. One and two axis prior art string encoders are shown in FIGS. 3 and 4, respectively. In FIG. 3, there is a single spring-loaded string 320 attached to an inspection head 310 and a scanner base 330. Again, the area to inspect 340 is larger than the coverage area. In FIG. 4, there are two spring-loaded strings 421 attached to an inspection head 410 and scanner bases 432. As in the three previous examples, the area to inspect 440 is larger than the device can cover in one positioning of the scanner base.

The inventors have developed a novel system for tracking and displaying the portions of a surface that have been scanned. The solution guarantees that the full surface will be covered with an adequate overlap and that indications are not missing. As the inventive system does not require a fixed reference point on the part under inspection nor any mechanical link between the scanning head and the part to be inspected, it is faster to deploy and does not limit operator agility.

DESCRIPTION

DETAILED SPECIFICATION

Figure 6:
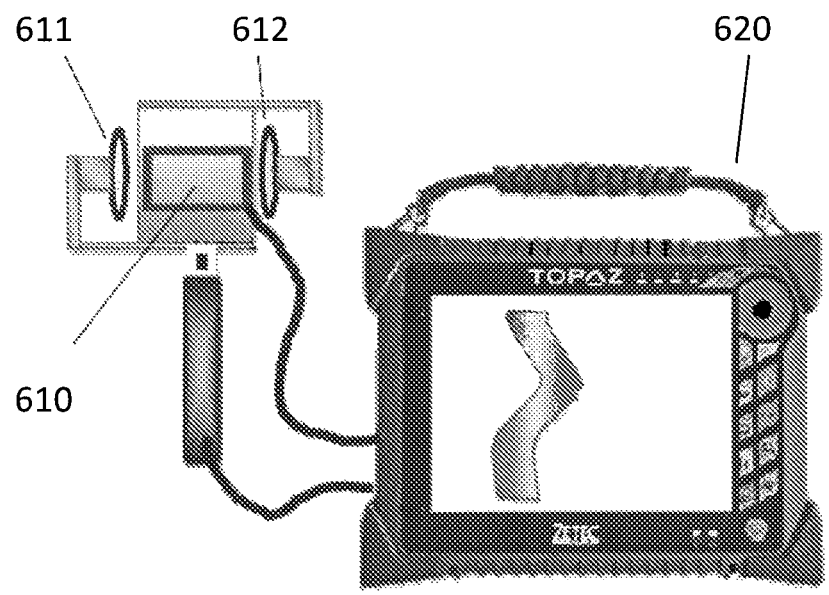
FIG. 6 is an exemplary system diagram.

As shown in FIG. 6, an inspection head 610, connected to an inspection computer 620 is provided with two position encoders 611, 612. Encoder 1 and 2 provide individual probe end position. Exemplary encoders can be of any kind, for example the known devised using a wheel, an image or time of flight. It is even possible to use dual axis (or more) encoders that give X and Y positions. As the probe is moved across a surface under test, the encoders provide position information that, among other things, is used to produce a display showing the area that has been traversed by the probe. A display is configured to "paint" the area under test with each subsequent area covered by the probe, so that the operator can ensure that the entire surface has been tested by observing the display to see that it is completely covered by the cumulative image produced by the scanner feedback.

To increase precision the system can also use more than two encoders. One possible combination is to use two pairs of two axis wheels (like an omni-wheel) or rolling spheres (like a mouse track ball) in a "X" pattern and have between 2 and 8 encoders positioned on the two axis wheels or rolling spheres.

Figure 1:
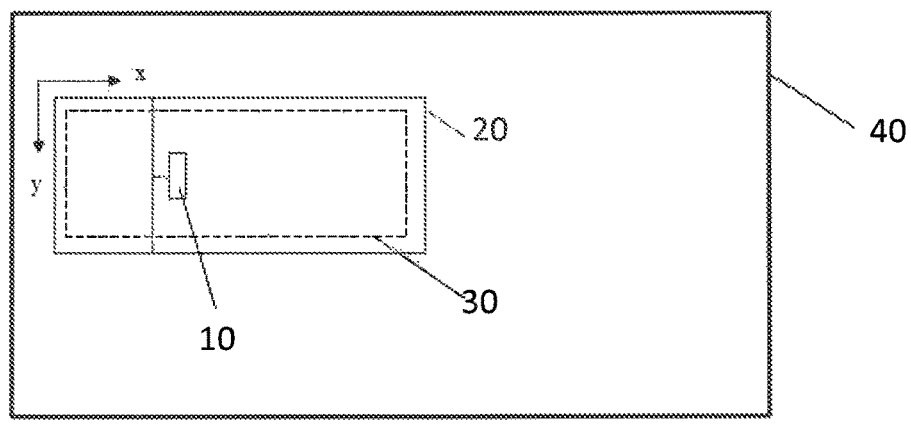
FIG. 1 is a prior art diagram of an are under test by an XY inspection head.
Figure 2:
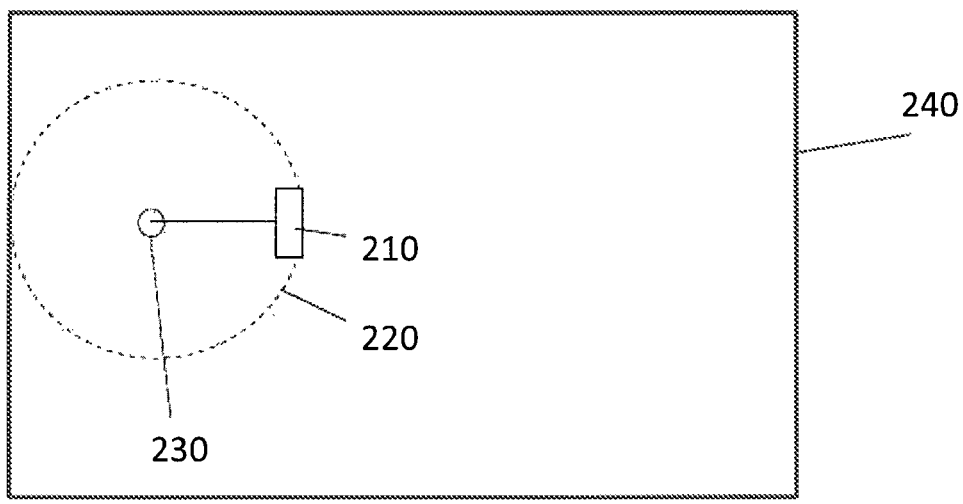
FIG. 2 is a prior art diagram of an area under test by a testing device for use on cylinders.
Figure 3:
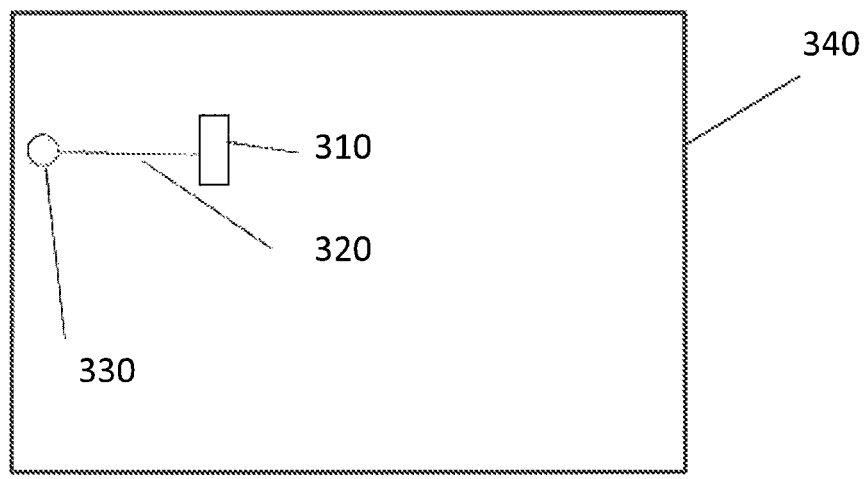
FIG. 3 is a prior art block diagram of a one axis string encoder.
Figure 4:
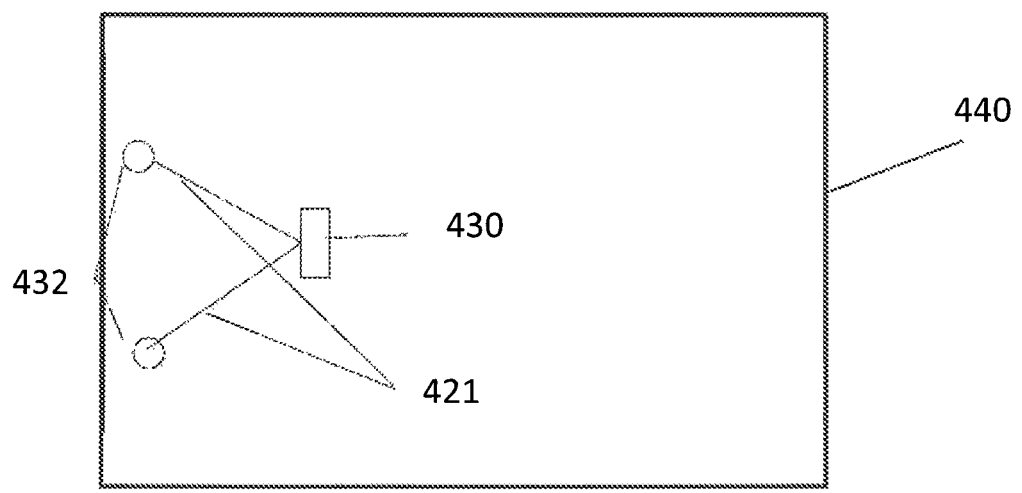
FIG. 4 is a prior art block diagram of a two axis string encoder.
Figure 5:
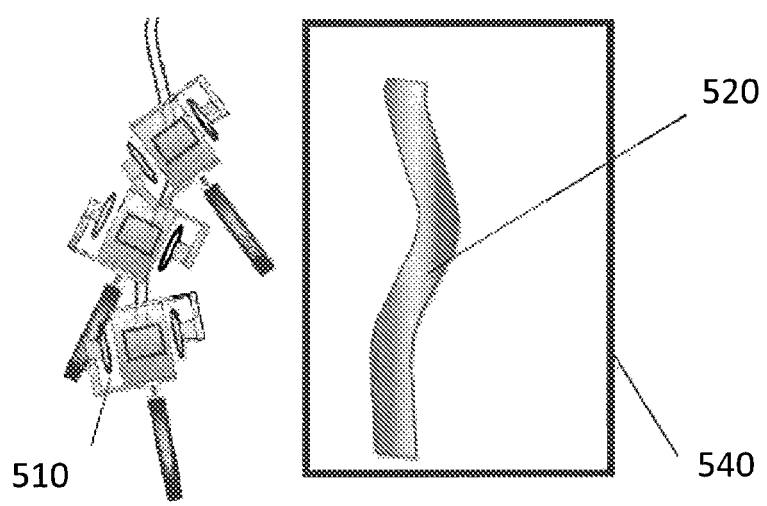
FIG. 5 is a drawing of an exemplary scanner and an exemplary display.

In an exemplary embodiment, shown in FIGS. 5 and 6, a non-destructive testing (NDT) scanner 510, 610 is fitted with movement encoders 611, 612. In an embodiment, the user must indicate to the system the starting point and initial direction of the scanner relative to the area to inspect. Once the scanner is moving, the encoders provide individual probe end positions allowing the system to calculate probe new position and orientation. If more than two encoders are used, then an average can be calculated for greater precision. FIG. 5 shoes a single scan track 520 in an area to inspect 540. FIG. 6 shows the indication of the scan track on the data acquisition device 620. With many encoders it can also be possible to reject aberrant values. The calculations can take place within the scanner, within the acquisition device or in an intermediate device. Calculations can be performed using any type of calculation device such as and not limited to FGPA, processors, DSP, micro-controllers. The positions and orientations are correlated with the NDT information and plotted on the acquisition device 620 screen as shown in FIG. 6.

By having encoders on two sides of an inspection head, as shown in FIG. 6, it is possible to know the orientation of the head, which does not have to be kept in a rectilinear path, as shown in FIG. 5.

The invention claimed is:

1. A non-destructive testing system for scanning the surface of an object under test comprising:
   a scanning head, said scanning head comprising at least two two-axis position encoders configured to provide position and orientation information, wherein said position and orientation information is averaged among the at least two two-axis position encoders; and a data acquisition device comprising a display configured to receive said averaged position and orientation information and to produce a cumulative display of portions of the object that have been scanned based on said averaged position and orientation information.

2. The non-destructive testing system of claim 1, wherein said scanning head comprises an ultrasonic transducer.

3. The non-destructive testing system of claim 1, wherein said scanning head is manually positioned about portions of the object under test.

4. The non-destructive testing system of claim 1, wherein said scanning head is robotically positioned.

5. The non-destructive testing system of claim 1, wherein said averaged position and orientation information is scanned for outlier data by said data acquisition device, and wherein said outlier data is not included in calculations of scanner head position.

6. A non-destructive testing scanning transducer for scanning the surface of an object under test comprising:

a scanning head, said scanning head comprising at least two two-axis position encoders configured to provide position and orientation information;

wherein said position and orientation information is scanned for outlier data by a data acquisition device comprising a display configured to receive said position and orientation information and to produce a cumulative display of portions of the object that have been scanned based on said position and orientation data not including said outlier data.

7. The non-destructive testing scanning transducer of claim 6, wherein said scanning head comprises an ultrasonic transducer.

8. The non-destructive testing scanning transducer of claim 6, wherein said scanning head is configured to be manually positioned about portions of the object under test.

9. The non-destructive testing scanning transducer of claim 6, wherein said scanning head is configured to be robotically positioned.

10. The non-destructive testing system of claim 6, wherein said position and orientation information is averaged among the at least two two-axis position encoders.

11. The non-destructive testing system of claim 6, wherein said outlier data is not included in calculations of scanner head position.

* * * * *